United States Patent [19]

Fox

[11] Patent Number: 4,500,658

[45] Date of Patent: Feb. 19, 1985

[54] RADIOPAQUE ACRYLIC RESIN

[75] Inventor: Adrian S. Fox, Denver, Conn.

[73] Assignee: Austenal International, Inc., Chicago, Ill.

[21] Appl. No.: 501,590

[22] Filed: Jun. 6, 1983

[51] Int. Cl.$^3$ .......................... C08K 3/10; C08K 5/54; C08K 5/06; A61K 5/06

[52] U.S. Cl. .................... 523/117; 524/762; 524/780; 524/783; 524/853; 524/854

[58] Field of Search ................ 523/117; 524/780, 783, 524/762; 106/35

[56] References Cited

U.S. PATENT DOCUMENTS

| | | | |
|---|---|---|---|
| 3,715,331 | 2/1973 | Molnar | 260/41 B |
| 3,925,895 | 12/1975 | Kliment et al. | 32/15 |
| 4,129,549 | 12/1978 | Kahane | 524/788 |
| 4,248,934 | 2/1981 | Wandel et al. | 523/222 |
| 4,264,489 | 4/1981 | Ibsen et al. | 523/115 |
| 4,302,376 | 11/1981 | Walkowiak et al. | 523/117 |
| 4,333,969 | 6/1982 | Wright et al. | 525/258 |
| 4,333,970 | 6/1982 | Bloomers et al. | 526/209 |
| 4,341,691 | 7/1982 | Anuta | 524/209 |
| 4,394,465 | 7/1983 | Podszun et al. | 523/116 |
| 4,403,065 | 9/1983 | Yoshioka et al. | 524/812 |

OTHER PUBLICATIONS

Derwent Abst., 55268 E/27, (06–1982), Dow EP-54832.
Derwent Abst., 05056 E/03, (12–1981), Kuraray KK, J56159271.
Derwent Abst., 04653 E/03, (12–1981), Nippon Synt., J56157417.
Derwent Abst., 09035 J/50 (02–1982), As UKR Phys. Chem., SV-907005.
Derwent Abst., 40125 K/17, (03–1983), J58045268, Nitto Elect.

*Primary Examiner*—Herbert J. Lilling
*Attorney, Agent, or Firm*—Lorraine Donaldson

[57] ABSTRACT

Biomedical radiopaque acrylic resin, in bead form, with an average diameter of from about 10 to 100 microns and having substantially uniformly dispersed throughout the bead about 5 to 50 wt. % of radiopaque inorganic pigment with an average particle size of about 0.1 to 20 microns.

9 Claims, No Drawings

RADIOPAQUE ACRYLIC RESIN

BACKGROUND OF THE INVENTION

This invention relates to novel radiopaque acrylic particles useful in the manufacture of biomedical devices. More particularly, it relates to the incorporation of radiopaque pigments in acrylic resins formed into beads through suspension polymerization which results in a uniform dispersion imparting a precise color control and radiopaque quality to acrylic particles useful for biomedical applications.

Radiopaque particles incorporated in biomedical devices and dental applications allow location of the device by X-ray examination. In particular, the removal and total retrieval of any injected, imbedded, or aspirated acrylic material after insertion arising from broken, damaged or displaced parts is facilitated by the use of radiopaque acrylic resin in the manufacture of the device. The site of such foreign bodies containing radiopaque particles can be quickly and conveniently located by X-ray examination.

In dental applications, a further advantage lies in the fact that the use of radiopaque material also allows for proper placement of dental bridges, and detection of voids and secondary caries. Also, improper contour and over-hangs can be detected and corrected, thereby eliminating broken, damaged or displaced parts.

Typically, in the prior art the radiopaque material has been incorporated into the biomedical device by use of colored heavy metal X-ray opaque compounds which are ball milled with the polymer beads or granules (U.S. Pat. No. 3,715,331) resulting in externally attached radiopaque pigment.

Also metal fillers, such as lead foil, silver alloy, gold and 1% powdered set amalgam have been used to render acrylic based biomedical material radiopaque. However, incorporation of such metal fillers causes stress concentrations at the interface between the insert and the resin which may weaken and fracture the material. Also, addition of the set amalgam produces a grey colored base which is esthetically undesirable.

Barium salts, such as barium sulfate, barium fluoride, barium polyacrylate and copolymers of barium acrylate and methyl methacrylate have also been used to supply radiopaque material. It has been found that increasing the barium sulfate level in the resin to 20% is necessary to render the resin sufficiently radiopaque. However, at this elevated level there is a negative impact on the strength of the acrylic material.

SUMMARY OF INVENTION

The present invention relates to a bio-medical radiopaque acrylic particle comprising a bead of acrylic resin having an average diameter of from about 10 to 100 microns and having substantially uniformly dispersed throughout the bead from about 5 to 50 wt. %, preferably 20 to 40 wt. %, of a radiopaque inorganic pigment having an average particle size of about 0.1 to 20 microns, with a preferred particle size of from about 0.8 to 3 microns.

Preferred acrylic resins are poly-(methyl methacrylate), poly-(ethyl methacrylate) and poly-(ethylene glycol dimethacrylate). The radiopaque pigment is preferably titanium dioxide, barium sulfate, zirconium dioxide or chromium oxide. Particularly preferred particles of this invention are those employing poly-(ethylene glycol dimethacrylate) as the resin and barium sulfate as the pigment, and those emloying poly-(methyl methacrylate) as the resin and zirconium dioxide as the pigment.

The present invention also includes a method of preparing radiopaque acrylic particles in bead form by substantially uniformly dispersing in an acrylic monomer from about 5 to 50 wt.% of radiopaque inorganic pigment, with an average particle size of from about 0.1 to 20 microns, an effective amount of a surfactant and a free radical forming polymerization initiator. Drops of the resulting monomer-pigment dispersion are then contacted with an aqueous solution containing an effective amount of a dispersant at a temperature of about 50° C. to 125° C., preferably 75° to 90° C. when polymerization of of the monomer in suspension occurs to form the preferred acrylic resin particles.

DETAILED DESCRIPTION OF THE INVENTION

Radiopaque acrylic resin particles of this invention are prepared by first substantially uniformly dispersing a radiopaque inorganic pigment in particulate form in the acrylic monomer. Suitable acrylic monomers include methyl methacrylate, ethyl methacrylate, ethylene glycol dimethacrylate and the like. Suitable radiopaque inorganic pigments, useful in the present invention, include titanium dioxide, zirconium dioxide, chromium oxide and barium sulfate. From about 5 to 50 wt. % of the particulate radiopaque pigment is incorporated in the monomer, preferably from about 20 to 40 wt. %. In order to insure a substantially uniform dispersion of pigment in the monomer material, it is preferable that the particle size of the pigment is from about 0.1 to 20 microns, preferably from about 0.8 to 3 microns. In a preferred procedure, the dispersion of the pigment in the monomer is aided by adding an appropriate amount of a surfactant, for example 0.50 to 5.0% based on the weight of the pigment. Suitable surfactants include sodium dioctyl sulfosuccinate, ethoxylated octylphenol, poly-(ethylene oxide-b-propylene oxide polyol, and alkylaryl poly-ether. If desired an effective amount, for example from about 0.5 to 5.0 wt. % of a silane coupling agent may be included. A suitable silane coupling agent is gamma-methacryloxy-propyl trimethoxysilane. From about 0.5 to 2.0 wt. % a free radical initiator based on weight of monomer is also added to the pigment-monomer mixture. Suitable free radical initiators include benzoyl peroxide, t-butyl peroctoate, or t-butyl perpivalate. The resulting pigment-monomer mixture is then agitated, for example by vigorously shaking or stirring the mixture to form a homogenous dispersion.

The pigment-monomer dispersion formed as described above is then added drop-wise to an aqueous solution containing a dispersant such as a methylcellulose typically in a concentration of about 0.05% to 0.50 wt. % based on the quantity of water used. By dropwise addition of the pigment-monomer dispersion is meant, addition of the pigment-monomer mixture in small discrete volumes for example from about 0.05 cc. to 0.5 cc., at a rate to provide for the addition of from about 1 cc. to 5 cc. per minute, preferably from about 2 cc. to 3 cc. per minute. During addition of the monomer-pigment mixture, the aqueous medium is maintained at a temperature of about 50° to 125° C., preferably 75° to 90° C., preferably under an inert gas such as nitrogen, and is vigorously agitated, for example by stirring with a mechanical stirrer at a speed of about 300 to 1000 r.p.m., preferably about 350 to 550 r.p.m., when polymerization of the monomer occurs. After addition of all the monomer-pigment dispersion, the aqueous suspension polymerization medium contains pigmented acrylic resin particles in the form of beads having an average diameter of about 10 to 100 microns with the radiopaque pigment substantially uniformly dispersed throughout the bead. Variations in the above described procedure will be well known to those skilled in the art and are within the scope of the present invention. Resin particles foamed as described above are readily recovered from the reaction medium by conventional means, for example by filtration and washing of the resin beads with water or other appropriate solvents.

The acrylic resin radiopaque pigmented particles of this invention may be used in biomedical applications by conventional procedures well known to those skilled in the art to conveniently and uniformly color biomedical materials and devices and provide for rapid X-ray detection thereof. For example, the radiopaque pigment may be used in the manufacture of biomedical devices, dentures, bone cement, and implants, for example, by casting or injecting molding. In such applications, the bead product may be used directly or the bead may be ground up to a desired particle size, admixed with other materials, and the like, as desired.

As an example radiopaque acrylic resin particles may be used in the manufacture of a denture by compounding 5–15% of the radiopaque acrylic resin particles with poly-(methyl methacrylate) powder and 1–5% benzoyl peroxide. This denture base powder is then formed into a dough by mixing with methyl methacrylate monomer at a 2:1 powder:liquid ratio. It can be compression molded in a preform denture flask containing gypsum dental stone and artificial teeth, and cured at elevated temperatures in a manner described in R. G. Craig, Editor, "Dental Materials: A Problem Oriented Approach," Mosby, 1978, pgs. 185–193.

The present invention is illustrated by the following examples. It will however, be understood that the invention is not limited to the specific details and conditions of these examples.

EXAMPLE I 747.5 g. of ethylene glycol dimethacrylate, 250 g. of barium sulfate, 2.5 g. of gamma-methacryloxypropyl trimethoxysilane (Silane A-174) were agitated under nitrogen purge for one hour at 3,200 rpm and room temperature and mixture of 7.19 g. of benzoyl peroxide (78%) and 2.5 g. of ethoxylated octylphenol (Sipronic ® F-400) were added to the mixture and the agitation was continued for an additional hour. This slurry was added drop-wise to an aqueous solution of 5 g. of methyl-cellulose (Methacel ® K-4M) in 3 liters of deionized water under a nitrogen purge and stirred at 375 rpm at a temperature of 75° C. Agitation and temperature were maintained at 45 minutes after completion of the addition of the pigment/monomer slurry at which time the temperature was raised to 95° C. and held there for one hour. The agitation was turned off and the acrylic beads were allowed to settle to the bottom of the flask. The supernatant liquid was drawn off and the beads were washed three times with two liters of deionized water, after which the beads were filtered and dried at 90° C. for twenty-four hours. An 87% yield of dried beads were obtained. The beads were ground to a 6 micron particle size powder containing 23% barium sulfate.

EXAMPLE II 743 g. of methyl methacrylate, 400.1 g. of zirconium oxide, 18.0 g. of benzoyl peroxide (78%), 4.0 g. of gamma-methacryloxypropyl trimethoxysilane (Silane A-174) and 8 g. of ethoxylated octylphenol (Sipronic ® F-400) were agitated at 3,000 rpm with a nitrogen purge for one hour. The monomer slurry was added drop-wise to a solution of 7.43 g. of methylcellulose (Methacel ® K-4M) in 3,000 ml. of deionized water at 70° C. under nitrogen purge and agitated at 500 rpm. The stirring was continued for two hours at 70° C. after the addition of the slurry was completed. The bead polymer was washed and dried as described in Example I. A yield of 73% acrylic bead polymer was obtained. The average unground particle size was 88 microns and the zirconium oxide content of the beads was 27%.

I claim:
1. A process for preparing a radiopaque acrylic particle in bead form comprising:
   (a) substantially uniformly dispersing in an acrylic monomer from about 5 to 50 wt.% of a radiopaque inorganic pigment having an average particle size of from about 0.1 to 20 microns, an effective amount of a surfactant and an effective amount of a free radical-forming polymerization initiator; and
   (b) contacting drops of the resulting monomer-pigment dispersion with an aqueous solution containing an effective amount of a dispersant at a temperature of from about 50° to 125° C. to polymerize said monomer.
2. The process of claim 1 wherein said inorganic pigment is selected from barium sulfate, titanium dioxide, zirconium dioxide, or chromium oxide.
3. The process of claim 1 wherein said pigment particle size is from about 0.8 to 3 microns.
4. The process of claim 1 wherein said monomer is selected from methyl methacrylate, ethyl methacrylate, and ethylene glycol dimethylacrylate.
5. The process of claim 1 wherein said temperature is from about 75° C. to 90° C.
6. The process of claim 1 wherein said surfactant is ethoxylated octylphenol.
7. The process of claim 1 wherein a silane coupling agent is additionally dispersed in said pigment-monomer dispersion.
8. The process of claim 7 wherein said coupling agent is gamma-methacryloxypropyl trimethoxy silane.
9. The radiopaque bead polymer produced by the process of claim 1.

* * * * *